(12) United States Patent
Chiou et al.

(10) Patent No.: US 8,182,844 B2
(45) Date of Patent: May 22, 2012

(54) **USE OF *CLERODENDRUM* SP. FOR TREATING TIC DISORDERS OR PSYCHIATRIC DISORDERS WITH SENSORIMOTOR GATING DEFICITS**

(75) Inventors: Lih-Chu Chiou, Taipei (TW); Pi-Chuan Fan, Taipei (TW); Wei-Jan Huang, Taipei (TW); Su-Jane Wang, Sinjhuang (TW)

(73) Assignees: National Taiwan University, Taipei (TW); Taipei Medical University, Taipei (TW); Fu Jen Catholic University, Sinjhuant, Taipei County (TW)

( * ) Notice: Subject to any disclaimer, the term of this patent is extended or adjusted under 35 U.S.C. 154(b) by 0 days.

(21) Appl. No.: 12/827,412

(22) Filed: Jun. 30, 2010

(65) Prior Publication Data
US 2011/0159129 A1   Jun. 30, 2011

(51) Int. Cl.
*A61K 36/00*   (2006.01)

(52) U.S. Cl. ........................................ 424/725; 424/774

(58) Field of Classification Search .................. None
See application file for complete search history.

(56) References Cited

OTHER PUBLICATIONS

DW ACC 2001-325051, Apr. 2001, Derwent or JP20, Katsurada et al.*
Murugesan et al. (Evaluation of psychopharmacological effects of *Clerodendrum phlomidis* Linn extract, Phytomedicine vol. 8(6), pp. 472-476, Nov. 2001).*
Kanchanapoom et al., "Megastigmane and iridoid glucosides from *Clerodendrum inerme*," (2001) Phytochemistry : 58 333-336.
Fan et al., "Intractable Chronic Motor Tics Dramatically Respond to *Clerodendrum inerme* (L) Gaertn," (Jul. 2009), J. of Child Neurology : 24(7).

* cited by examiner

*Primary Examiner* — Christopher R Tate
*Assistant Examiner* — Randall Winston
(74) *Attorney, Agent, or Firm* — Volpe and Koenig, P.C.

(57) ABSTRACT

The present invention relates to the use of a composition made from *Clerodendrum* for treating tic disorder or sensorimotor gating deficits, wherein the composition is particularly made from the leaves of the plant.

11 Claims, 3 Drawing Sheets

(A)

(B)

(A)

(B)

USE OF *CLERODENDRUM* SP. FOR TREATING TIC DISORDERS OR PSYCHIATRIC DISORDERS WITH SENSORIMOTOR GATING DEFICITS

FIELD OF THE INVENTION

The present invention relates to the use of *Clerodendrum* sp. for treating tic disorders or psychiatric disorders with sensorimotor gating deficits.

BACKGROUND OF THE INVENTION

Tics are involuntary, sudden, rapid, repetitive, non-rhythmic, stereotyped movements or phonic productions (*Lancet Neurol.* 2005; 4:149-159). Patients usually are aware of nearly irresistible somatosensory urges that precede the tics. These urges likely reflect a defect in sensorimotor gating because they intrude into the child's conscious awareness and become a source of distraction and distress (*J Child Neurol.* 2006; 21:642-629). Motor tics range from brief, meaningless motor fragments involving one muscle group (i.e. simple tics) to a more coordinated sequence of movements that last longer and appear as a non-purposeful or more goal-directed action (i.e. complex tics). A diagnosis of chronic tic disorder is made for those with either motor or phonic tics, but not both, continuously or intermittently for more than one year (*Semin Pediatr Neurol.* 2006; 13:231-242). Several lines of evidence support an abnormality of dopaminergic system in Tourette's syndrome, an idiopathic illness with multiple motor and at least one vocal tics, lasting for at least 1 year before age 21, including the therapeutic response of neuroleptics and the morphological data from postmortem and nuclear imaging studies (*Pediatric Neurology: Principles and Practice*, $4^{th}$ ed. Philadelphia, Pa.: Mosby-Elesevier; 2006:887-903; and *Brain Dev.* 2003; 25:S70-S84). Clinically, dopamine D2-receptor blockers and dopamine depletors are thought to be the most effective anti-tic treatment (*Expert Opin Emerg Drugs.* 2005; 10:365-380). However, these treatments are suboptimal in terms of effectiveness and side effects, such as body weight gain, extrapyramidal symptoms and exacerbations of anxiety (*J Child Neurol.* 2006; 21:690-700). In addition to typical neuroleptics, several pharmacological interventions have also been proposed, including atypical neuroleptics, $\alpha_2$-agonists, central nervous system stimulants, selective serotonin reuptake inhibitors, opiates, benzodiazepines, and nicotine. Conversely, dopamine agonists sometimes improve tics or Tourette's syndrome.

*Clerodendrum* sp. is a shrub belonging to Verbenaceae and widely distributed in South and Southeast Asia, Australia and Pacific islands. The root and leaf extracts of the plants such as *Clerodendrum inerme* have been reported to be used as a folk medicine in the treatment of various diseases such as coughs, serofulous infection, pyretic, buboes problem, venereal infections and skin disease and beriberi disease, and also as a vermifuge (*Phytochemistry.* 2001; 58:333-336). However, no scientific literatures or reports indicate that this local herb is useful in relieving symptoms of neurological or psychiatric disorders such as sensorimotor gating deficits or tic attacks.

BRIEF SUMMARY OF THE INVENTION

The present invention is based on the unexpected finding that *Clerodendrum* sp. possess anti-tic activity and are effective in treating sensorimotor gating deficits.

Accordingly, the present invention relates to a method for treating tic disorders or psychiatric disorders with sensorimotor gating deficits comprising administering to a subject in need thereof a composition made from *Clerodendrum* sp.

The various embodiments of the present invention are described in details below. Other characteristics of the present invention will be clearly presented by the following detailed description about the various embodiments and claims.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Figure 1:
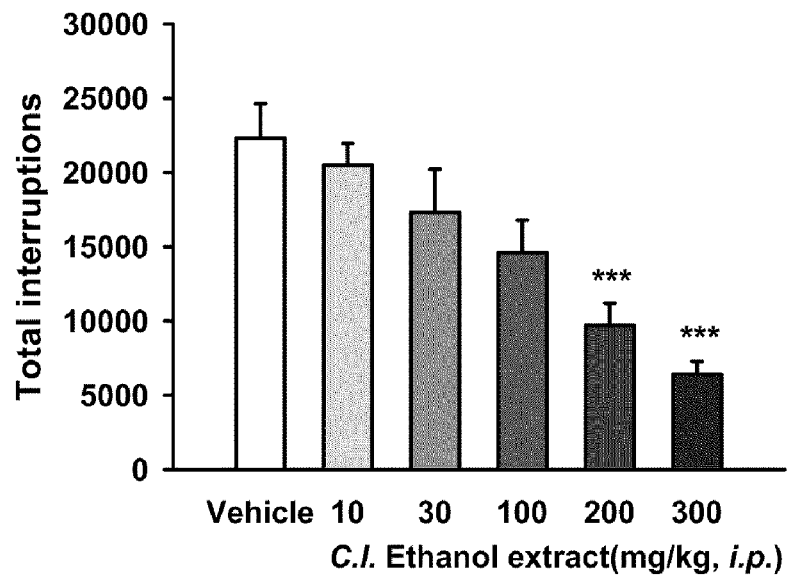
FIG. 1 shows the effects of an ethanol extract of *Clerodendrum inerme* on the motor functions of mice. The ethanol extract was administered by i.p. injection 15 min before subjecting to various tests, including locomotor activity (A), and grip strength test (B). The total locomotor activity was measured at 2 hours after injection of methamphetamine, 2 mg/kg.
Figure 1:
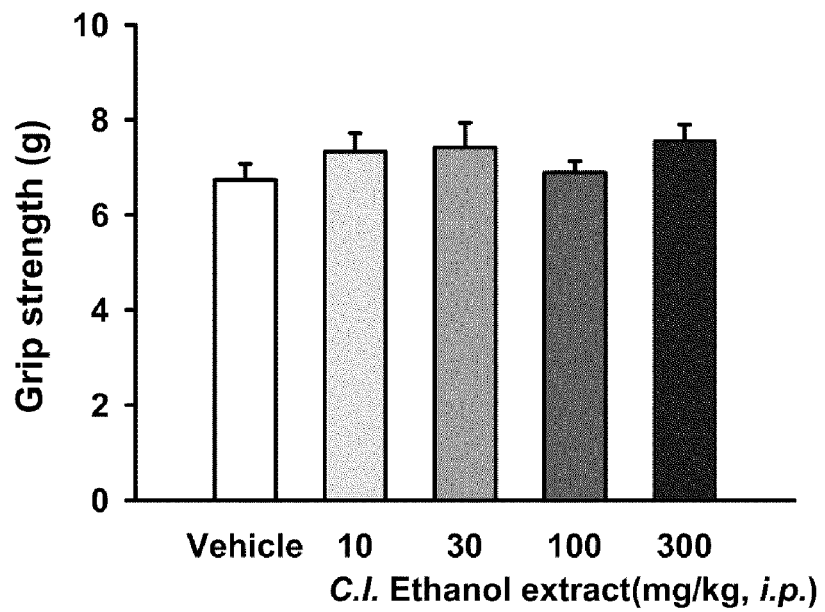

Unless defined otherwise, all technical and scientific terms used herein have the meaning commonly understood by a person skilled in the art to which this invention belongs.

The articles "a" and "an" are used herein to refer to one or more than one (i.e., at least one) of the grammatical object of the article.

Described herein is the use of *Clerodendrum* sp. for treating tic disorders or psychiatric disorders with sensorimotor gating deficits. As shown in the examples below, in one case report, we found that a 13-year-old girl, with chronic motor tic disorder refractory to multiple anti-tic therapies, who showed dramatic improvement after taking the leaf juice of *Clerodendrum inerme*; no side effects were observed during a follow-up of more than 6 years. On the other hand, in an animal model treated with methamphetamine, an ethanol extract of *Clerodendrum inerme* was found to decrease methamphetamine-induced hyperlocomotion but not affect the normal motorer functions of the mice as revealed by the grip test. In addition, such ethanol extract of *Clerodendrum inerme* was also found to rescue the disruption of prepulse inhibition of the startle response (PPI) induced by methamphetamine (2 mg/kg) and ketamine (30 mg/kg), the animal models based on dopamine and glutamate hypotheses, respectively. It was also effective in MK-801 (0.3 mg·kg)-induced PPI disruption, another animal model based on glutamate hypothesis.

Accordingly, the present invention provides a method for treating tic disorders or psychiatric disorders with sensorimotor gating deficits comprising administering to a subject in need thereof a composition made from *Clerodendrum inerme*.

The term "*Clerodendrum* sp." used herein refers to any plant in the genus of *Clerodendrum*, which is a shrub belonging to Verbenaceae and widely distributed in South and Southeast Asia, Australia and Pacific islands. *Clerodendrum* sp. includes at least *Clerodendrum bungei*, *Clerodendrum philipinum*, *Clerodendron trichotomum*, *Clerodendrum quadriloculare*, *Clerodendrum capitatum*, *Clerodendrum indicum L.*, *Clerodendron phlomidis*, and *Clerodendrum inerme*. Specifically, the plant as used herein is *Clerodendrum indicum L. Clerodendron phlomidis*, and/or *Clerodendrum inerme*, more specifically *Clerodendrum inerme*.

"A composition made from *Clerodendrum* sp." as used herein refers to any product or composition made from the plant per se, its part(s), such as leaves, flowers, roots, seeds, stems and fruits, or any modified forms thereof such as juice, powders, granules, extracts, slices, concentrates, and precipitates.

In one embodiment, the composition of the invention comprises juice from *Clerodendrum* sp. Specifically, the juice is from leaves of the plant.

A composition made from *Clerodendrum* sp. as described herein can be prepared by any standard method or techniques commonly known in the art. Typically, *Clerodendrum* sp. or parts thereof are washed and air-dried, cut or chopped and then mixed or soaked with a proper solvent which includes but is not limited to water, methanol, ethanol, propanol, iso-propanol, butanol, iso-butanol and the like. Additional steps for concentration such as evaporation or those for purification such as filtration, centrifugation and chromatography may be subsequently performed.

In one example, the leaves of *Clerodendrum* sp. are chopped and mixed with water (e.g. by a blender), the solid residue is removed by filtration, and the juice thus obtained is collected.

In another example of the invention, the leaves of *Clerodendrum* sp. are extracted by a solvent such as ethanol. Particularly, the leaves of the plant are washed and air dried, subjected to cutting or grinding, and then mixed or soaked with ethanol for a period of time, such as 2 to 10 days, more particularly 5 to 8 days. The soaking or mixing step may be repeated as needed. The ethanol fraction(s) is then harvested and combined together. The ethanol fraction thus obtained can be further concentrated or purified if necessary.

The term "treating" as used herein refers to the application or administration of a composition including one or more active agents to a subject afflicted with a disorder, a symptom of the disorder, or a predisposition toward the disorder, with the purpose to cure, heal, alleviate, relieve, alter, remedy, ameliorate, improve, or affect the disorder, the symptoms of the disorder, the disabilities induced by the disorder, or the predisposition toward the disorder. An "effective amount" is an amount of a composition that is capable of producing a medically desirable result as described above in a treated subject. For example, an effective amount of the composition according to the invention for treating tic disorders or psychiatric disorders with sensorimotor gating deficits is an amount sufficient to reduce or ameliorate the symptoms of tic disorders or psychiatric disorders with sensorimotor gating deficits as compared to the symptoms manifested in the absence of the composition.

According to the invention, a composition made from *Clerodendrum* sp. can be used to treat a subject who is afflicted with tic disorders. As described above, tic disorders are involuntary, sudden, rapid, repetitive, non-rhythmic, stereotyped movements or phonic productions, ranging from brief, meaningless motor fragments involving one muscle group (i.e. simple tics) to a more coordinated sequence of movements that last longer and appear as a non-purposeful or more goal-directed action (i.e. complex tics).

In addition, the composition according to the invention can also be used to treat psychiatric disorders with sensorimotor gating deficits, which are characterized clinically by a loss in the normal ability to automatically suppress or "gate" irrelevant information in cognitive, sensory, or motor domains. Sensorimotor gating deficits have been reported in patients with neuropsychiatric disorders such as schizophrenia (*Psychophysiology* 15:339-343), Tourette syndrome ("TS", 2001, *Biol Psychiatry* 50:578-585), obsessive compulsive disorder ("OCD", 2005, *Biol Psychiatry* 57:1153-1158), attention deficit hyperactivity disorder ("ADHD", *Psychopharmacology* (*Berl*) 165:118-127), adults with autism (*Biol Psychiarty* 2007, 61:482-486) or bipolar disorder (*Acta Psychiatr Scand* 2008; 117:313-318) Intrusive sensory information appears to be particularly disruptive of cognitive processing in schizophrenia (*Br J Med Psychol* 1961; 34: 103-116), and of motor function in Tourette Syndrome (TS) (*Am J Psychiatry* 1993; 150: 98-102; *J Clin Psychiatry* 2000; 61: 150-156). PPI disruption has been established as a measure in animals and humans reflecting the deficit of sensorimotor gating function. (*Psychopharmacology* (*Berl*) 199:331-388).

To facilitate delivery, the composition of the invention can be further formulated into a pharmaceutical composition with a suitable pharmaceutically acceptable carrier. "Pharmaceutically acceptable" as used herein means that the carrier is compatible with the active ingredient contained in the composition of the invention, preferably capable of stabilizing the active ingredient, and not deleterious to the subject to be treated. The carrier may serve as a diluent, vehicle, excipient, or medium for the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The composition of the invention can be formulated so as to provide quick, sustained or delayed release of the active ingredient after administration to the patient by employing procedures known in the art.

The composition according to the invention can be in the form of tablets, pills, powders, lozenges, sachets, cachets, elixirs, suspensions, emulsions, solutions, syrups, soft and hard gelatin capsules, suppositories, sterile injectable solutions, and packaged powders.

The composition of the invention may be delivered through any physiologically acceptable route such as orally, parentally (e.g. intramuscularly, intravenously, subcutaneously, interperitoneally), transdermally, rectally, by inhalation and the like. In one embodiment, the composition of the invention is orally administrated.

The dose of the composition of the present invention may vary with factors such as the route of administration, the size and species of the subject to receive the agent, and the purpose of the administration. The dose in each individual case may be determined empirically by a skilled artisan according to the disclosure herein and established methods in the art.

The present invention will now be described more specifically with reference to the following embodiments, which are provided for the purpose of demonstration rather than limitation.

Example 1

Preparation of an Extract of *Clerodendrum inerme*

*Clerodendrum inerme* were harvested in mangrove marshes in the riverside of Taiwan. The leaves were collected and air dried. The dried leaves (3.0 kg) were grinded and repeatedly extracted with 95% EtOH (10 L) three times, for each of which extraction the leaves were soaked in ethanol for about one week. The combined EtOH layers were evaporated under reduced pressure to give a residue (246 g) which was used to conduct the subsequent animal experiments.

Example 2

Effect of the Extract of *Clerodendrum inerme* on the Motor Functions of Mice 2.1 Animal Male ICR mice (25-35 g) mice were used for behavioral studies. They were bred, housed and maintained in the animal facility center with temperature- and humidity-controlled and 12:12 light dark cycle in National Taiwan University, College of Medicine (NTUMC). All animal experiments were carried out in accordance with the guidelines established by the Institutional Animal Care and Utilization Committee of NTUMC.

2.2 Motor function Methamphetamine (2 mg/kg) was injected into mice to induce hyperlocomotion in the mice as a typical model for behavioral experiments. After injection of methamphetamine, the mice were administrated by i.p. injection of vehicle (0.1 ml dimethylsulfoxide) or the C.I. extract at a range of doses from 10 to 300 mg/kg. After 15 minutes, the treated mice were then subjected to tests for locomotor activity and grip strength, respectively.

The locomotor activity of the mouse was monitored from the disruptions of infra-red photobeans in the locomotor cage of Photobeam Activity System (San Diego Instrument, San Diego, Calif.). The grib strength was measured by the grib force of the forepaws of the mouse with Grip Strength System (San Diego Instrument, San Diego, Calif.).

As shown in FIG. 1, the ethanol extract of *Clerodendrum inerme* leaves (10-300 mg/kg, i.p.) dose-dependently decreased methamphetamine-induced hyperlocomotor activity in 6-9 week-old ICR mice (FIG. 1A); however, it did not affect the normal motor functions of mice as reveled by the grip tests (FIG. 1B).

2.3 Prepulse Inhibition of the Startle Response (PPI)

PPI is a neurophysiological phenomenon that the startle response to a stimulus, which could be a sound, an airpuff or a light, is inhibited if a stimulus with the same source but at weaker intensity prior to the stimulus was applied within a short interval. This is a fast neuroadaptative system to protect the living organisms from startle stimulation. It is believed to be a processing protection in a living organism that PPI serves as a sensorimotor gating, a pre-conscious regulator of attention, to reduce the startle response which is harmful to the information professing. It is known that such sensorimotor gating is impaired in patients with various neuropsychiatric disorders, including schizophrenia, obsessive compulsive disorder (OCD), attention deficit hyperactivity disorder (ADHD) or Tourette syndrome (TS), a spectrum of motor tic disorders. PPI can be assessed by the motor response in either humans (measuring the eyeblink response by electromyograph) or animals (measuring the startle response).

2.3.1 Animal Model Based on Dopamine Hypothesis

Mice were i.p. injected by methamphetamine (2 mg/kg) to induce PPI disruption, as a schizophrenia model based on dopamine hypothesis. PPI was measured using the SR-LAB Startle Response System (San Diego Instrument, San Diego, Calif.). The treated mice were individually placed in a startle enclosure in the startle chamber with a background white noise of 65 db and left undisturbed for 10 min. Then a 16-min session was started that consisted of 56 trials. Each trial started with a 50-ms null period, followed by a 20 ms prepulse white noise of 71 or 77 db. After a 100 ms delay, the startle stimulus was presented (a 40 ms 115 dB white noise), followed by a 290-ms recording time. The total duration of the trial was 500 ms. Eight types of trials was given below: prepulse (71 or 77 db) plus startle (10 trials perprepulse intensity), prepulse (71, or 77 db) alone (4 trials per prepulse intensity), startle alone (10 trials), and no stimulation (4 trials). In the no-stimulation trials, baseline measurements were taken. In the startle-alone trials, the basic auditory startle was measured, and in the prepulse-plus-startle trials, the amount of inhibition of normal startle induced by the prepulse was measured and expressed as a percentage of the basic startle. In the prepulse-alone trials, the normal response to a weak noise was measured as a control.

Figure 2:
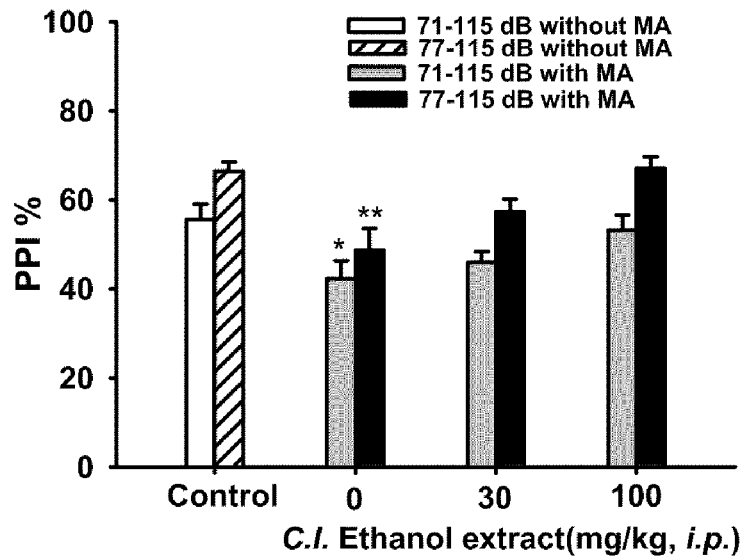
FIG. 2 shows the effect of an ethanol extract of *Clerodendrum inerme* (A) and diazepam (B) on rescue of methamphetamine (2 mg/kg)-induced disruption of prepulse inhibition (PPI) of the startle response in mice. The PPI was measured by the inhibition of the startle response of the mouse in response to a 115 dB acoustic stimulation when a prepulse acoustic stimulation at 71 dB or 77 dB was applied, as compared to the startle response without prepulse stimulation. *$p<0.05$, $p<0.01$, *$p<0.001$ vs. Control (without methamphetamine).
Figure 2:
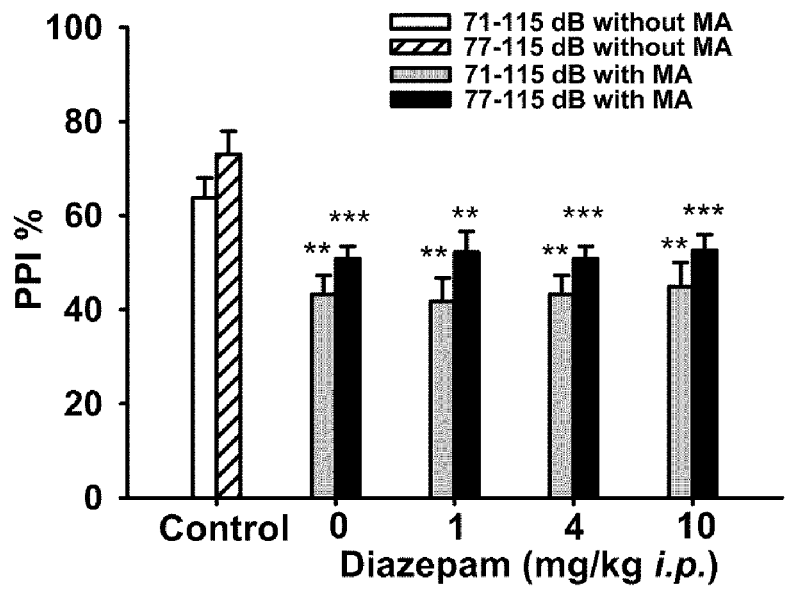

FIG. 2A shows the results. In the control mice, the startle response to a 115 db acoustic stimulation was inhibited by a prepulse stimulation with 71 db by (ie. the PPI was) 55.6±3.5% (open bar). However, in animal treated with methamphetamine (the first gray bar without the C.I. ethanol extract), the PPI was reduced to 42.4±4.1%. Increasing the prepulse stimulus to 77 db, the PPI was increased (slashed bar) while methamphetamine also reduced the PPI of the response to 77 db prepulse (the first black bar without the C.I. ethanol extract). Interestingly, the C.I. ethanol extract (30-100 mg/kg, i.p.) was effective in rescuing methamphetamine-induced PPI disruption in response to both 71 and 77 db prepulse stimuli (the second and third gray/black bars).

Further, diazepam, a known antiseizure agent, was administered to the mice to test if the agent affected methamphetamine-induced PPI disruption. As shown in FIG. 2B, diazepam did not rescue methamphetamine-induced PPI disruption.

2.3.2 Animal Model Based on Glutamate Hypothesis

In addition to dopamine hypothesis, overactive glutamatergic transmission is one of the contributors to the pathogenesis of schizophrenia. Accordingly, mice were i.p. injected with ketamine (30 mg/kg) or MK-801 (dizocilpine) (0.3 mg/kg), the N-methyl-D-aspartate (NMDA) channel blockers which block NMDA glutamate receptor, to induce PPI disruption, as schizophrenia models based on glutamate hypothesis. The treated mice were subjected to the startle response test and PPI measurement according to the procedure as above-described.

Figure 3:
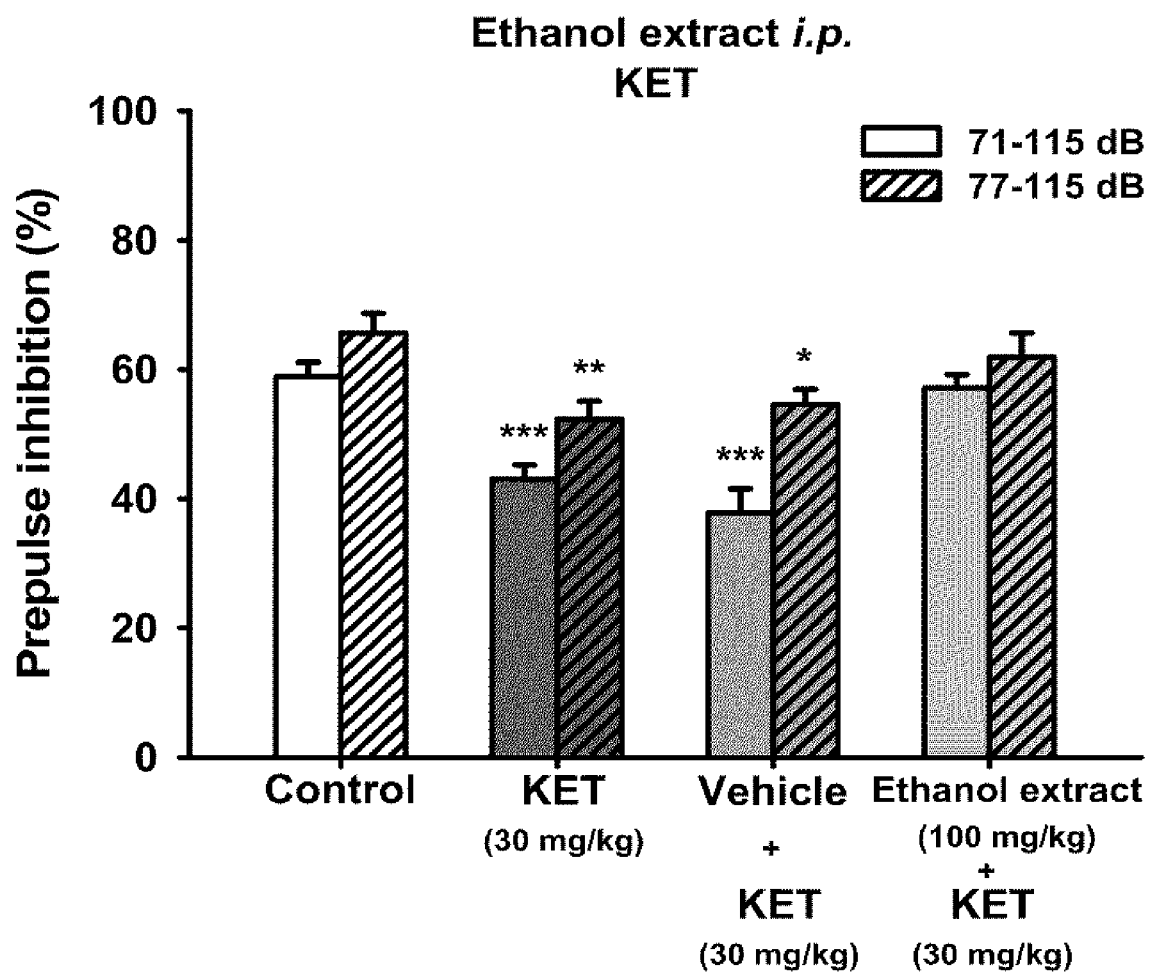
FIG. 3 shows the effect of an ethanol extract of *Clerodendrum inerme* on rescue of ketamine (KET, 30 mg/kg)-induced disruption of prepulse inhibition (PPI) of the startle response in mice. The PPI was measured by the inhibition of the startle response of the mouse in response to a 115 dB acoustic stimulation when a prepulse acoustic stimulation at 71 dB or 77 dB was applied, as compared to the startle response without prepulse stimulation. *$p<0.05$, $p<0.01$, *$p<0.001$ vs. Control (without ketamine).

FIG. 3 shows the result. PPI disruption was induced by i.p. injection of 30 mg/kg of ketamine, and *Clerodendrum inerme* ethanol extract, when given by i.p. (100 mg/kg, n=8) injection, reinstated the PPI disruption induced by ketamine. In addition, *Clerodendrum inerme* ethanol extract also effectively reinstated the PPI disruption induced by MK-801 (0.3 mg/kg) (data not shown). It is shown that *Clerodendrum inerme* ethanol extract produced similar improvement as it did in the methamphetamine-treated model.

Taken together, these results suggest that *Clerodendrum inerme* ethanol extract can rescue PPI disruption in schizophrenia models based on dopamine and glutamate theories.

Example 3

Effect of the Extract of *Clerodendrum inerme* in One Case Report

A 13-year-old girl was admitted to National Taiwan University Hospital (NTUH) due to intractable, rhythmic 3-Hz jerky movements of four limbs for four months. Her actions were insuppressible and lasted for hours with consciousness preserved. She also complained of dizziness, headaches and nausea. No aura or triggered factors were noted. She had visited the outpatient clinic of another medical center where haloperidol was increased in dosage and diazepam was added, but in vain. The electroencephalography and brain computed tomography at that hospital were negative. Tracing the past history, this patient had been healthy until age 2, when she suffered from right frontal skull fracture, without intracranial hemorrhage, due to trauma. She started to develop focal epilepsy and was treated with regular antiepileptic drugs. The regimen was shifted to lamotrigine and clonazepam after age 7, when she experienced status epilepticus. After this episode, the patient started to have occasional complex motor tics, and haloperidol and alprazolam were used.

On admission, her consciousness was clear. She had a mask face and bradykinesia, in addition to persistent shaking of four limbs, which subsided during sleep. Her daily medications were haloperidol (5 mg bid), alprazolam (0.5 mg bid), biperiden (1.5 mg bid) and lamotrigine (25 mg bid). On physical and neurological examination, her temperature was 36.5° C., with a blood pressure of 99/58 mm Hg, a heart rate of 88 beats per minute and a respiratory rate of 20 breaths per minute. Her consciousness was clear with intact judgement, orientation, memory, abstract thinking, and calculation. Her cranial nerves, deep tendon reflexes, muscle power and sensory functions were also intact. Finger-nose-finger test revealed coarse tremor and mild dysmetria. Nerve conduction velocity, somatosensory evoked potential and repeated electroencephalography revealed normal results. Serum copper, ceruloplasmin, electrolytes, and 24-hour urine copper levels were all within normal limits. Brain magnetic resonance imaging was negative. A diagnosis of chronic motor tic disorder, complicated with extrapyramidal syndrome resulting from haloperidol, was made. Her mask face, bradykinesia and tremor disappeared after we discontinued haloperidol and adjusted the regimen to lamotrigine (25 mg bid), clonazepam (2 mg bid), and alprazolam (0.5 mg bid). She was discharged and followed up at our clinic thereafter. However, her involuntary movements, including wave-like shaking of the trunk or repeated fisting and opening of hands, relapsed one week later. Her actions were very strong to shake where she sat, lasting for several hours with consciousness preserved. Risperidone was carefully titrated (up to 3 mg qd), along with haloperidol (5 mg bid), but in vain. She started to have chronic psychological disorder and had a problem in dealing with her male classmates, who often teased her. Several medications, including olanzapine, clonidine, pergolide, sulpiride and biperidal, were tried without success, and prominent weight gain was noted (from 45 to 70 kg). The IQ test was 68, classified as mild mental retardation, while she took multiple anti-tic, including high-dose antipsychotics, and antiepileptic drugs. However, her symptoms remained variable, with strong shaking of the limbs or trunk, or abdominal wall every day in a waxing and waning course, which made her absent from school. Withholding all medications for 1 day, she received examination of catecholamine metabolites in the cerebrospinal fluid. The results revealed low homovanillic acid, (81.46 nM; normal: 211-540 nM) and low 5-hydroxyindoleacetic acid (38.62 nM; normal: 95-173 nM), the metabolites of dopamine and serotonin, respectively. The homovanillic acid/5-hydroxyindoleacetic acid ratio was normal (2.11; normal: 1.8-4.0).

Subsequently, this patient, at age 14 years, 8 months, started to take the extract of the grounded leaves of *Clerodendrum inerme*, which was prepared by mixing the leaves with water by a blender and collecting the juice after filtration as resulted. Her tics subsided dramatically an hour later after taking one dose of the extract, which was made from 50 pieces of large leaves or 100 pieces of small leaves, mixed with 100 ml water (500 mg/ml). Honey was added because of the bitter taste. Initially, she took the extract twice a week to keep herself symptom-free and then, the interval was prolonged gradually to once per 2-6 months when her tics recurred. All the medications were discontinued at age 14 years, 10 months, except lamotrigine (50 mg bid) and clonazepam (0.5 mg bid), both of which failed to be successfully tapered off due to relapse of epilepsy with hallucinations. At age 16 years, 9 months, serial examinations of her hemograms, liver and renal functions, blood gas and electrolytes were within normal limits. No obvious side effects were observed clinically. The follow-up IQ test had been arranged, but the patient was absent on the examination day. She was leading a normal school life at the regular class of a senior high school and had been well for more than 3 years after taking the extract.

This patient followed up regularly in NTUH pediatric outpatient clinic for her seizure problem. At age 19, this patient in her recent visit (May 31, 2010) described that her motor tics, which attack in variable patterns once for a while (2-4 times a month), subsided after having this herb extract. This suggests a human subject has taken this leaf juice for up to 6 years without significant side effects.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. A method for treating tic disorders comprising administering to a subject in need thereof a composition comprising an effective amount of a *Clerodendrum inerme* extract.

2. The method of claim 1, wherein the extract comprises juice from *Clerodendrum inerme*.

3. The method of claim 1, wherein the extract comprises leaf juice from *Clerodendrum inerme*.

4. A method for treating psychiatric disorders with sensorimotor gating deficits comprising administering to a subject in need thereof a composition comprising an effective amount of a *Clerodendrum inerme* extract.

5. The method of claim 4, wherein the extract comprises juice from *Clerodendrum inerme*.

6. The method of claim 4, wherein the extract comprises leaf juice from *Clerodendrum inerme*.

7. The method of claim 4, wherein the extract is obtained from the leaves of *Clerodendrum inerme* by a solvent.

8. The method of claim 7, wherein the solvent is ethanol.

9. The method of claim 4, wherein the psychiatric disorders are schizophrenia, obsessive compulsive disorder (OCD), attention deficit hyperactivity disorder (ADHD), Tourette syndrome (TS), autism, or bipolar disorder.

10. The method of claim 1, wherein the composition is administered orally.

11. The method of claim 4, wherein the composition is administered orally.

* * * * *